United States Patent
Duftler et al.

(10) Patent No.: US 10,181,012 B2
(45) Date of Patent: *Jan. 15, 2019

(54) EXTRACTING CLINICAL CARE PATHWAYS CORRELATED WITH OUTCOMES

(71) Applicant: INTERNATIONAL BUSINESS MACHINES CORPORATION, Armonk, NY (US)

(72) Inventors: Matthew J. Duftler, Mahopac, NY (US); Jianying Hu, Bronx, NY (US); Geetika T. Lakshmanan, Winchester, MA (US); Szabolcs Rozsnyai, New York, NY (US); Fei Wang, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/204,628

(22) Filed: Jul. 7, 2016

(65) Prior Publication Data
US 2016/0321405 A1   Nov. 3, 2016

Related U.S. Application Data

(63) Continuation of application No. 13/851,755, filed on Mar. 27, 2013, now Pat. No. 9,430,616.

(51) Int. Cl.
*G06G 7/48*        (2006.01)
*G06F 19/00*       (2018.01)
(Continued)

(52) U.S. Cl.
CPC ...... *G06F 19/325* (2013.01); *G06F 17/30589* (2013.01); *G06F 17/30598* (2013.01);
(Continued)

(58) Field of Classification Search
CPC ............ G06F 19/3443; G06F 19/3437; G06F 17/30598; G06F 9/46; G06Q 50/24; H05K 999/00
(Continued)

(56) References Cited

U.S. PATENT DOCUMENTS

2002/0022973 A1   2/2002   Sun et al.
2003/0216939 A1   11/2003  Bito et al.
(Continued)

FOREIGN PATENT DOCUMENTS

JP   2006228150   8/2006
JP   2012043113   1/2012
(Continued)

OTHER PUBLICATIONS

Aalst, W. "Using Real Event Data to X-Ray Business Processes Helps Ensure Conformance Between Design and Reality" Communications of the ACM. vol. 55, No. 8. Aug. 2012. pp. 76-83.
(Continued)

*Primary Examiner* — Andre Pierre Louis
(74) *Attorney, Agent, or Firm* — Tutunjian & Bitetto, P.C.; Rabin Bhattacharya (57) ABSTRACT

Systems and methods for data analysis include constructing patient traces as a set of medical events for each patient of a patient population, the patient population being segmented based on patient outcomes. Medical events in one or more of the patient traces are reduced to provide processed patient traces. The processed patient traces are clustered to identify a cluster of patient traces. A process model is mined, using a processor, representing an aggregation of treatment pathways in the patient traces from the cluster. Patterns from patient traces are identified that are discriminative of patient outcomes. At least one of the patterns is represented with
(Continued)

respect to the process model to identify treatment pathways correlated with the patient outcomes.

20 Claims, 4 Drawing Sheets

(51) Int. Cl.
    *G06F 17/30*      (2006.01)
    *G16H 50/50*      (2018.01)
    *G16H 50/70*      (2018.01)

(52) U.S. Cl.
    CPC ............ *G06F 19/00* (2013.01); *G16H 50/50* (2018.01); *G16H 50/70* (2018.01)

(58) Field of Classification Search
    USPC ........................................................ 703/2, 6
    See application file for complete search history.

(56) References Cited

U.S. PATENT DOCUMENTS

| | | |
|---|---|---|
| 2008/0306894 A1 | 12/2008 | Rajkumar et al. |
| 2009/0262131 A1 | 10/2009 | Suntinger et al. |
| 2009/0265288 A1 | 10/2009 | Chakravarty et al. |
| 2010/0131253 A1* | 5/2010 | Benayon ............ G06F 17/5009 703/6 |
| 2010/0131434 A1 | 5/2010 | Magent et al. |
| 2011/0166883 A1 | 7/2011 | Palmer et al. |
| 2011/0185230 A1 | 7/2011 | Agrawal et al. |
| 2012/0150498 A1 | 6/2012 | Shastri et al. |
| 2012/0232926 A1 | 9/2012 | Boyle et al. |
| 2012/0253841 A1 | 10/2012 | Erlandsen et al. |
| 2012/0290319 A1 | 11/2012 | Saria et al. |
| 2013/0275149 A1* | 10/2013 | Gaines .................. G06F 19/325 705/3 |
| 2013/0339060 A1 | 12/2013 | Delaney et al. |
| 2014/0280075 A1 | 9/2014 | Huang et al. |

FOREIGN PATENT DOCUMENTS

| | | |
|---|---|---|
| WO | WO0057264 A1 | 9/2000 |
| WO | WO2006132320 A1 | 8/2006 |

OTHER PUBLICATIONS

Aiolli, F., et al. "Metric for Clustering Business Processes Based on Alpha Algorithm Relations" Department of Pure and Applied Mathematics, University of Padua, Italy. 2011. (pp. 1-17).
Bose, R., et al. "Context Aware Trace Clustering: Towards Improving Process Mining Results" Proceedings of the SIAM International Conference on Data Mining, SDM 2009. Apr./May 2009. pp. 401-412.
Cheng, H., et al. "Direct Discriminative Pattern Mining for Effective Classification" Proceedings of the 24th International Conference on Data Engineering, ICDE 2008. Apr. 2008. (10 Pages).
Ester, M., et al. "A Density-Based Algorithm for Discovering Clusters in Large Spatial Databases With Noise" Proceedings of 2nd International Conference on Knowledge Discovery and Data Mining. 1996. (6 Pages).
Greco, G., et al. "Mining Expressive Process Models by Clusteringworkflow Traces" Proceedings Advances in Knowledge Discovery and Data Mining, 8th Pacific-Asia Conference, PAKDD 2004. May 2004. pp. 52-62.
Hall, P., et al. "Choice of Neighbor Order in Nearest-Neighbor Classification" The Annals of Statistics. vol. 36, No. 5. 2008. pp. 2135-2152.
Hartmann, B., et al. "Review of Antibiotic Drug Use in a Surgical ICU: Management With a Patient Data Management System for Additional Outcome Analysis in Patients Staying More Than 24 Hours" Clinical Therapeutics. vol. 26, No. 6. Apr. 2004. pp. 915-924.
Huang, Z., et al. "On Mining Clinical Pathway Patterns From Medical Behaviors" Artificial Intelligence in Medicine. vol. 56, No. 1. Sep. 2012. pp. 1-16.
Jung, J., et al. "Workflow Clustering Method Based on Process Similarity" International Conference Computational Science and Its Applications—ICCSA 2006. May 2006. pp. 379-389.
Kastner, M., et al. "Heuristic Methods for Searching and Clustering Hierarchical Workflows" 12th International Conference Computer Aided Systems Theory—EUROCAST 2009. Feb. 2009. (8 Pages).
Lakshmanan, G., et al. "Leveraging Process Mining Techniques to Analyze Semi-Structured Processes" IT Professional. IEEE computer Society Digital Library. IEEE Computer Society. Aug. 2012. pp. 1-13.
Lo, D., et al. "Mining Closed Discriminative Dyadic Sequential Patterns" EDBT 2011, 14th International Conference on Extending Database Technology. Mar. 2011. pp. 1-12.
Qiao, M., et al. "Towards Efficient Business Process Clustering and Retrieval: Combining Language Modeling and Structure Matching" Business Process Management—9th International Conference, BPM 2011. Sep. 2011. pp. 199-214.
Rebuge, A., et al. "Business Process Anaylsis in Heathcare Environments: A Methodology Based on Process Mining" Information Systems. vol. 37, No. 2. Apr. 2012. pp. 1-18.
Sartipi, K., e al. "Mined-Knowledge and Decision Support Services in Electronic Health" International Workshop on Systems Development in SOA Environments, 2007. May 2007. (6 Pages).
Silva, V. et al. "Similarity-Based Workflow Clustering" Journal of Computational Interdisciplinary Sciences 2(1): 23-35. Jan. 2011. pp. 23-35.
Song, M., et al. "Trace Clustering in Process Mining" Business Process Management Workshops, BPM 2008 International Workshops. Sep. 2008. pp. 1-12.
Weijters, A., et al. "Process Mining With the Heuristicsminer Algorithm" Beta Working Paper Series, WP 166, Eindhoven University of Technology, Eindhoven, 2006.
Non-Final Office Action for U.S. Appl. No. 13/851,675 mailed on Feb. 25, 2015.
Office Action dated May 28, 2015 for U.S. Appl. No. 13/851,618.
Final Office Action for U.S. Appl. No. 13/851,618 mailed on Oct. 7, 2015.
Final Office Action for U.S. Appl. No. 14/030,652 mailed on Oct. 7, 2015.
Non-Final Office Action for U.S. Appl. No. 13/966,664 mailed on Oct. 26, 2015.
Office Action dated Mar. 28, 2016 for U.S. Appl. No. 13/851,618.

* cited by examiner

FIG. 4

EXTRACTING CLINICAL CARE PATHWAYS CORRELATED WITH OUTCOMES

BACKGROUND

1. Technical Field

The present invention relates to analysis of patient data, and more particularly to extracting clinical care pathways correlated with outcomes.

2. Description of the Related Art

Identifying care pathways correlated with patient outcomes from patient event data is important for gaining insight into which care pathways will lead to positive or negative outcomes. Once identified, such care pathways could be used to refine care plan descriptions for treating particular diseases, such as congestive heart failure. However, real world raw patient event data suffers from a number of potential problems. For example, it is common for multiple events to occur concurrently, causing pattern explosion. Another problem is that the diversity of events could be explosive. These problems may cause loops and spaghetti-like patterns in the patient event data when a process model is mined. Existing process mining approaches do not correlate clinical pathways with patient outcomes. In addition, there is no existing research that provides for the overlay of clinical pathways correlated with patient outcomes on a mined model of patient event traces.

SUMMARY

A method for data analysis includes constructing patient traces as a set of medical events for each patient of a patient population, the patient population being segmented based on patient outcomes. Medical events in one or more of the patient traces are reduced to provide processed patient traces. The processed patient traces are clustered to identify a cluster of patient traces. A process model is mined, using a processor, representing an aggregation of treatment pathways in the patient traces from the cluster. Patterns from patient traces are identified that are discriminative of patient outcomes. At least one of the patterns is represented with respect to the process model to identify treatment pathways correlated with the patient outcomes.

A system for data analysis includes a medical records database configured to construct patient traces stored on a computer readable storage medium as a set of medical events for each patient of a patient population, the patient population being segmented based on patient outcomes. A trace preprocess module is configured to reduce medical events in one or more of the patient traces to provide processed patient traces. A cluster module is configured to cluster the processed patient traces to identify a cluster of patient traces. A pathway extraction module is configured to mine a process model representing an aggregation of treatment pathways in the patient traces from the cluster. A pattern extraction module is configured to identify patterns from patient traces that are discriminative of patient outcomes. A visual interface is configured to represent at least one of the patterns with respect to the process model to identify treatment pathways correlated with the patient outcomes.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

In accordance with the present principles, systems and methods for extracting clinical care pathways correlated with outcomes are provided. Patient traces are constructed as sets of medical events for each patient. The patient traces are preprocessed to reduce events in the patient traces and thereby reduce complexity. Preprocessed patient traces are then clustered and a cluster is identified, such as, e.g., the largest cluster, to remove patient outliers. Process mining is performed to mine a process model representing aggregated clinical treatment pathways from the patient traces of the cluster. Discriminative patterns are mined, e.g., from the preprocessed patient traces to identify patterns that are discriminative of patient outcomes. The discriminative patterns are overlaid on the process model to identify clinical pathways that are correlated with a particular patient outcome.

The present principles provide a visual overlay of discriminative patterns with respect to the process model to enable a user to identify one or more discriminative patterns in the context of the end-to-end clinical care pathways. One advantage of the present principles is that a user can identify the key clinical practice pathways that are correlated with positive or negative outcomes on the mined model. Insight can be obtained by comparing and contrasting separate overlays of clinical practice pathways correlated to positive and negative patient outcome.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Figure 1:
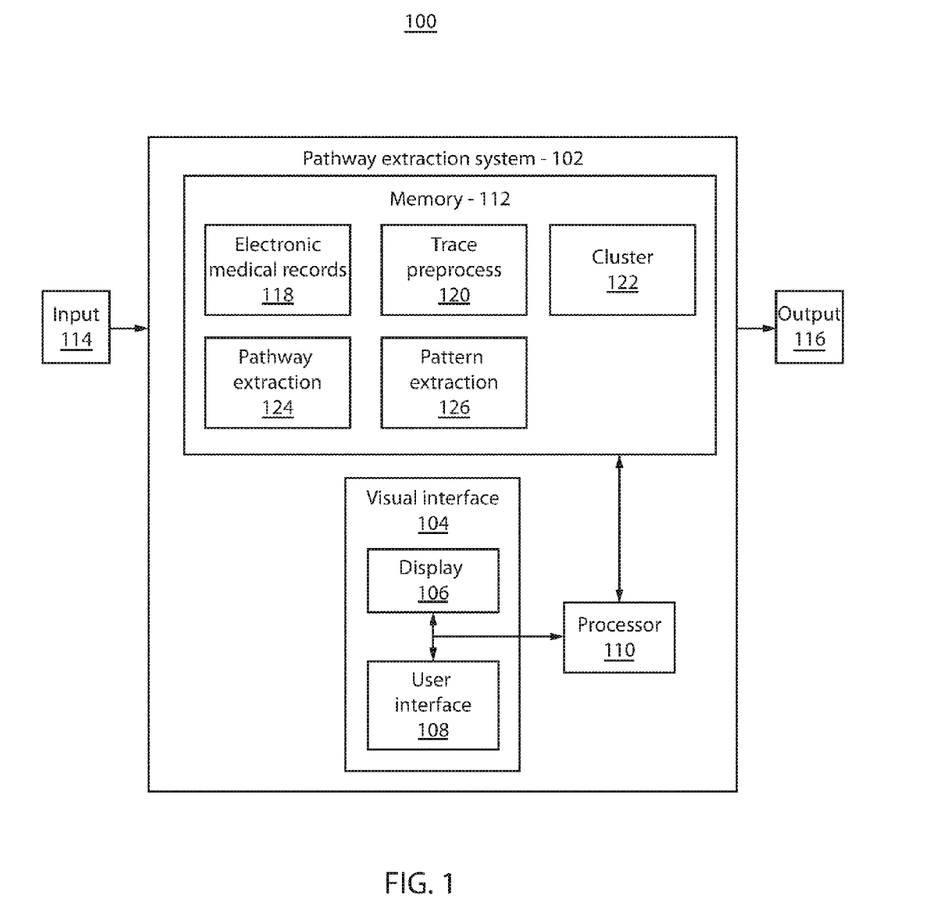
FIG. 1 is a block/flow diagram showing a system/method for extracting clinical care pathways correlated with patient outcomes, in accordance with one illustrative embodiment.

Referring now to the drawings in which like numerals represent the same or similar elements and initially to FIG. 1, a block/flow diagram showing a system for extracting clinical care pathways correlated with patient outcomes 100 is illustratively depicted in accordance with one embodiment. The system 100 may analyze data (e.g., patient data) to identify care pathways correlated with patient outcomes.

While the present principles are described in terms of healthcare, it should be understood that the present principles are not so limited. Rather, other applications are also contemplated within the scope of the present principles, such as, e.g., insurance.

The system 100 may include a system or workstation 102. The system 102 preferably includes one or more processors 110 and memory 112 for storing patient data, applications, modules and other data. The system 102 may also include a visual interface 104, which may include one or more displays 106 for viewing. The displays 106 may permit a user to interact with the system 102 and its components and functions. This may be further facilitated by a user interface 108, which may include a mouse, joystick, or any other peripheral or control to permit user interaction with the system 102 and/or its devices. It should be understood that the components and functions of the system 102 may be integrated into one or more systems or workstations.

The system 102 may receive input 114, which may include, e.g., health care event data for a cohort of patients stored in a medical records database, such as, e.g., electronic medical records (EMR) 118. The patient cohort may be defined by a user (e.g., physician). For example, the patient cohort may include outputs of risk stratification procedures. Health care event data may include patient demographics, physician notes, immunizations, radiology reports, etc. EMR 118 hierarchically stores health care event data as medical events, such as, e.g., medications, labs, diagnoses, vital signs, etc., as well as patient outcomes. The patient cohort may be segmented by outcome according to criterion, e.g., into positive and negative outcomes. For example, patients not hospitalized for congestive heart failure one year after diagnosis may be a positive outcome, while patients hospitalized for congestive heart failure within one year after diagnosis may be a negative outcome. Other types of segmentation may also be employed. A patient trace is constructed for each patient as a set of ordered events (e.g., chronologically) leading to a patient outcome. Each patient trace may include attributes for each event, such as, e.g., event names, event timestamps, etc.

Trace preprocess module 120 is configured to preprocess the patient traces due to the big data nature of medical records. Trace preprocess module 120 reduces the number of events in a patient trace by performing, e.g., filtering, aggregating events of a concurrent event and consolidating consecutive identical events. Other forms of preprocessing are also contemplated.

Trace preprocess module 120 may be configured to filter the patient traces. Patient data are hierarchically stored in EMR 118 in terms of medical events. For example, diagnosis events may be stored as a diagnosis hierarchy involving the levels, from highest to lowest: hierarchy name, Hierarchical Condition Categories (HCC) code, Diagnosis (DX) group names and the International Classification of Diagnosis 9th Edition (ICD9). In another example, medication events may be stored in a medication hierarchy, involving the levels, from highest to lowest: pharmacy class, pharmacy subclass and ingredient. Other hierarchical arrangements are also applicable. Trace preprocess module 120 filters patient traces by replacing event names with its hierarchical categorical name to reduce the diversity of events. Hierarchical categorical names may be obtained from the EMR 118, ontologies, etc. Trace preprocess module 120 may also filtering out events by type or attribute, etc. For example, all medication names may be replaced by its Pharmacy Subclass name, all diagnoses names may be replaced by DX group Names, lab events may be filtered to include labs for congestive heart failure, etc. Other types of filtering may also be implemented.

Trace preprocess module 120 may also be configured to aggregate events of a concurrent event. Due to resolution limits of temporal data (e.g., one day) in EMR 118, patient traces often involve complex events. Other time periods are also contemplated. For example, during a day, a patient may encounter multiple medical events. These medical events occurring within a same day are treated as same day concurrent events (SDCEs) due to the resolution of temporal data. However, increasing numbers of events within an SDCE may lead to a dramatic increase in patient traces, as all combinations of events must be accounted for. To address this issue of pattern explosion, trace preprocessing module 120 aggregates the events of the SDCEs into super events. In this way, the number of events in an SDCE is reduced.

First, clinical event packages are identified from each SDCE (e.g., using frequent itemset mining). Clinical event packages are sets of events that have a certain frequency of occurrence among all SDCEs. A two-way sorting approach is then applied to aggregate events within SDCEs as super events based on the identified clinical event packages. Clinical event packages identified from an SDCE are first sorted according to cardinality. Clinical event packages with a same cardinality are then sorted by appearance frequency. The clinical event package having a longest cardinality is selected as a super event. Where multiple clinical event packages have the same longest cardinality, the clinical event package with the same longest cardinality that has a highest appearance frequency is selected as the super event. This process is repeated for the remaining events in the SDCE. By grouping events within an SDCE as super events, the number of events in an SDCE is thereby reduced.

Trace preprocess module 120 may further be configured to remove or consolidate consecutive identical events. Consecutive identical events may suggest some routine check or periodical treatment and therefore these events may be treated similarly. However, the temporal event patterns of repeating events are not as informative. Consecutive identical events can be removed or consolidated to eliminate event self-loops in detected patterns. Consolidated consecutive identical events may be distinguished by, e.g., adding the prefix "Rep," adding the suffix "-Repeat," etc. For example, vital events occur for a same patient consecutively can be consolidated as Vital-Repeat in the patient's trace.

Cluster module 122 is configured to cluster the preprocessed patient traces to identify a dominant set of similar patient traces to thereby remove patient outliers. In one embodiment, for example, where there is a small amount of data, the cluster module 122 may be skipped and the preprocessed patient traces may proceed to pathway extraction module 124. Cluster module 122 clusters patient traces based on their execution similarity. The execution of a patient trace refers to the set and order of medical events, such as, e.g., medications, labs, vitals, and diagnoses. Patient traces are transformed into string-based representations and a density-based clustering is applied using a string edit-distance metric.

In one embodiment, patient traces are transformed into strings by mapping all known event types to, e.g., Unicode characters. Table 1 shows an exemplary mapping of event types to characters.

TABLE 1 exemplary mapping of event types to Unicode characters.

| Event Type | Mapped Character |
| --- | --- |
| OrderReceived | A |
| ShipmentCreated | B |
| TransportStarted | C |
| TransportEnded | D |
| InvoiceIssued | E |

Each event in each patient trace (T1, T2, . . . , Tn) is then replaced with the corresponding mapped character. The ordering of the resulting string representation of each patient trace corresponds to the ordering of events for that patient trace (e.g., by time). Table 2 shows an exemplary string representation of patient traces according to the mapping of Table 1. Each patient trace in its string representation is now considered to be a point and handled to compute patient trace clusters.

TABLE 2 exemplary string representation of patient traces.

| Trace | String Representation |
| --- | --- |
| OrderReceived → ShipmentCreated → TransportStarted → TransportEnded → InvoiceIssued | ABCDE |
| OrderReceived → ShipmentCreated → TransportStarted → ShipmentCreated → TransportStarted → . . . | ABCBC |

Clustering may include performing, e.g., DBSCAN (density-based spatial clustering of applications with noise), k-nearest neighbor clustering (k-NN), etc. Other clustering approaches may also be employed. The results are one or more clusters of patient traces that share a similar behavior. Clustering receives one or more parameters (e.g., epsilon) as an input indicating the maximum distance between points allowable in a cluster.

Pathway extraction module 124 is configured to mine a process model from the patient traces of a cluster. Preferably, the process model is mined from the largest cluster. However, the process model may be mined from other clusters, such as, e.g., clusters that include a number of patient traces that meet or exceed a threshold amount, etc. Based on patient traces of medical events, models can be extracted that describe underlying processes. A business process model shows a specific ordering of work activities with a beginning, an end, and clearly indicated inputs and outputs. In one embodiment, a process model can be represented in terms of a Petri net, which is a formal, graphical, executable technique for the specification and analysis of concurrent, discrete-event dynamic systems. In another embodiment, a process model can be represented as a Business Process Modeling Notation (BPMN). Other representations may also be employed.

The process model in accordance with the present principles is an aggregation of patient traces to form a model of aggregated clinical patient treatment pathways from all relevant patient traces. An artificial start event and artificial end event are injected in each patient trace. This allows the resulting mined process model to include start and end nodes. The start event may be given a timestamp that occurs before the earliest event in that patient trace. The end event may be given a timestamp that occurs after the last event in the patient trace. Pathway extraction module 124 mines process models by applying, e.g., the HeuristicMiner technique. The HeuristicsMiner technique addresses mining of traces that could be incomplete and may contain noise. HeuristicMiner computes an edge frequency (a number between 0 and 1) to indicate the confidence in an edge. HeuristicMiner provides a number of heuristic rules that rely on the frequency of edges to infer ordering relations that determine the semantics of the underlying process model captured by the traces. Other process mining techniques are also contemplated.

Figure 2:
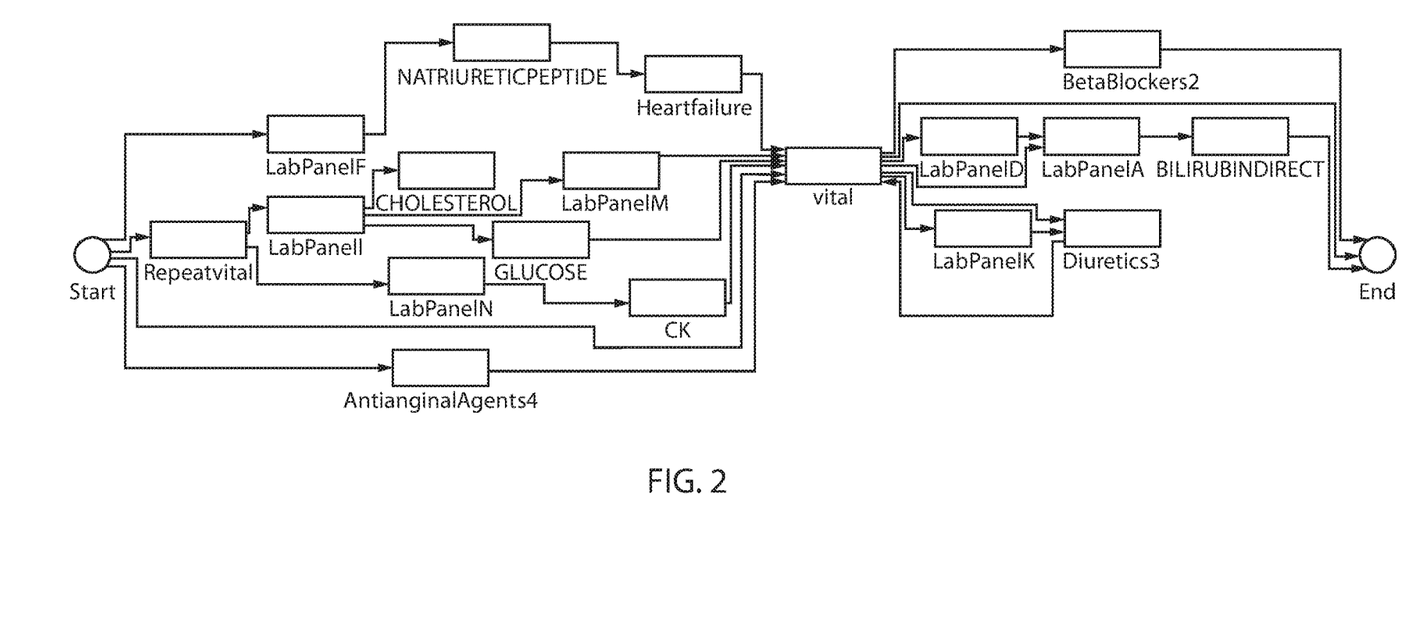
FIG. 2 shows an exemplary process model, in accordance with one illustrative embodiment.

Referring for a moment to FIG. 2, an exemplary process model is shown in accordance with one illustrative embodiment. Events include, e.g., lab panels (LabPanelA, LabPanelB, etc.), medications (AntianginalAgents4, BetaBlockers2, Biuretics3, etc.) and diagnoses (heartfailure). Events are represented as nodes. Dependencies between nodes are represented as edges. The process model has a start and end node to indicate the start and end of aggregation of treatment pathways.

Referring back to FIG. 1, pathway extraction module 124 may also refine the process model to alter the complexity of the process model (e.g., according to a preferred graph density or scarcity). Process model refinement may include varying the dependency measure or the minimum number of observations. Other process model refinements may also be employed.

Process model refinement may include varying the dependency measure. The dependency edge between repeating event node pairs is defined based on the dependency measure (e.g., threshold). Repeating event node pairs refers to two event nodes connected by an edge, occurring multiple times regardless of the direction of dependency of the edge. For repeating event node pairs, the dependency edge between the two event nodes is defined by comparing the frequency of occurrence of directions of dependencies for all repeating event node pairs to a threshold. For example, given repeating event node pairs A and B, the frequency of occurrence of (A→B) is compared with the frequency of occurrence of (B→A). If the frequency of occurrence of (A→B) exceeds (B→A) by a predefined threshold, the dependency edge between event nodes A and B is represented as (A→B). Similarly, if the frequency of occurrence of (B→A) exceeds (A→B) by a predefined threshold, the dependency edge between event nodes A and B is represented as (B→A).

Process model refinement may include varying the threshold on the minimum number of observations identified in process mining to display a node. For example if the threshold on the minimum number of observations is specified as 10, then at least 10 patient traces must contain a node, for that node to be shown in the process model mined by the mining algorithm. Every time the threshold on the minimum number of observations is changes, the process model is mined again from the traces.

Pattern extraction module 126 is configured to extract patterns from the preprocessed patient traces (from trace preprocess module 120) and identify the patterns that are discriminative for a patient outcome. Pattern extraction 126 may be performed separately (e.g., in parallel, successively, etc.) from pathway extraction 124. One goal of extracting discriminative patterns is to detect frequent patterns from the patient traces such that the patterns are frequent and discriminative. Patterns should be frequent in that they should appear in a certain portion of the patient population. Patterns should also be discriminative in that they should be correlated for different outcomes.

Pattern extraction module 126 receives preprocessed patient traces from trace preprocess module 120 and outputs a set of identified patterns. Pattern extraction module 126 may apply any subsequence mining technique, such as, e.g., prefixScan or SPAM (sequential pattern mining). Pattern mining may be based on an inputted support value to specify how frequent the final detected patterns are to be. Pattern extraction module 126 mines patterns from patient traces with different outcomes and identifies patterns that are frequent with one type of outcome but scarce with the other.

Patterns may be represented as bag-of-pattern vectors for each patient trace. First, patterns are organized into a pattern dictionary of a size m, where m is the number of different event patterns in the patient trace. The bag-of-pattern vector for each patient trace is an m-dimensional vector, where the value of the i-th dimension represents the frequency of occurrence of the i-th event corresponding to a patient trace.

Often times, pattern mining results in a large number of patterns. As such, the constructed bag-of-pattern representations may be very sparse, since most patterns do not occur most of the time. However, if vectors are too sparse, computational models may not be meaningful. Pattern extraction module 126 may apply hierarchical pattern summarization to compress the pattern set.

Hierarchical pattern summarization merges detected pattern pairs in a hierarchical (or recursive) way. A pattern pair may be merged as a single pattern, and the dependency between events may be ignored. A pattern pair refers to a pair of patterns having the same events, but different (e.g., opposite) dependency edge directions. For example, if (A→B) is a detected pattern, and (B→A) is also a detected pattern, then the patterns (A→B) and (B→A) can be merged as a single pattern (A;B) and the order between them can be ignored. The bag-of-pattern vector representation of the resultant pattern after merging has frequencies that are equal to the sum of the individual patterns it merged from. Hierarchical pattern summarization can be repeated for all pattern pairs.

Pattern extraction module 126 identifies discriminative patterns for a patient outcome by outcome analysis, which may include, e.g., sparse logistic regression, etc. Patterns may be extracted from the set of preprocessed patient traces (i.e., from trace preprocess module 120), from a cluster of patient traces (i.e., from cluster module 122), etc. The extracted patterns are preferably preprocessed to filter the patterns before outcome analysis is performed. Filtering may be based on, e.g., odds ratio, information gain, etc.

Visual interface 104 is configured to visually represent the process model (from pathway extraction 124) and discriminative patterns (from pattern extraction 126) as an output 116. The visual interface 104 may involve one or more displays 106 and/or user interfaces 108. Preferably, the top k discriminative patterns are overlaid over the mined model, where k is any positive integer specified by a user. Discriminative patterns are distinguished from the process model, e.g., by color. Discriminative patterns may also be distinguished to indicate patient outcome (e.g., green for positive outcome, red for negative outcome, etc.). Other representations of the discriminative patterns are also contemplated, such as, e.g., line thickness, highlights, box, dimming areas outside the discriminative patterns, etc.

Figure 3:
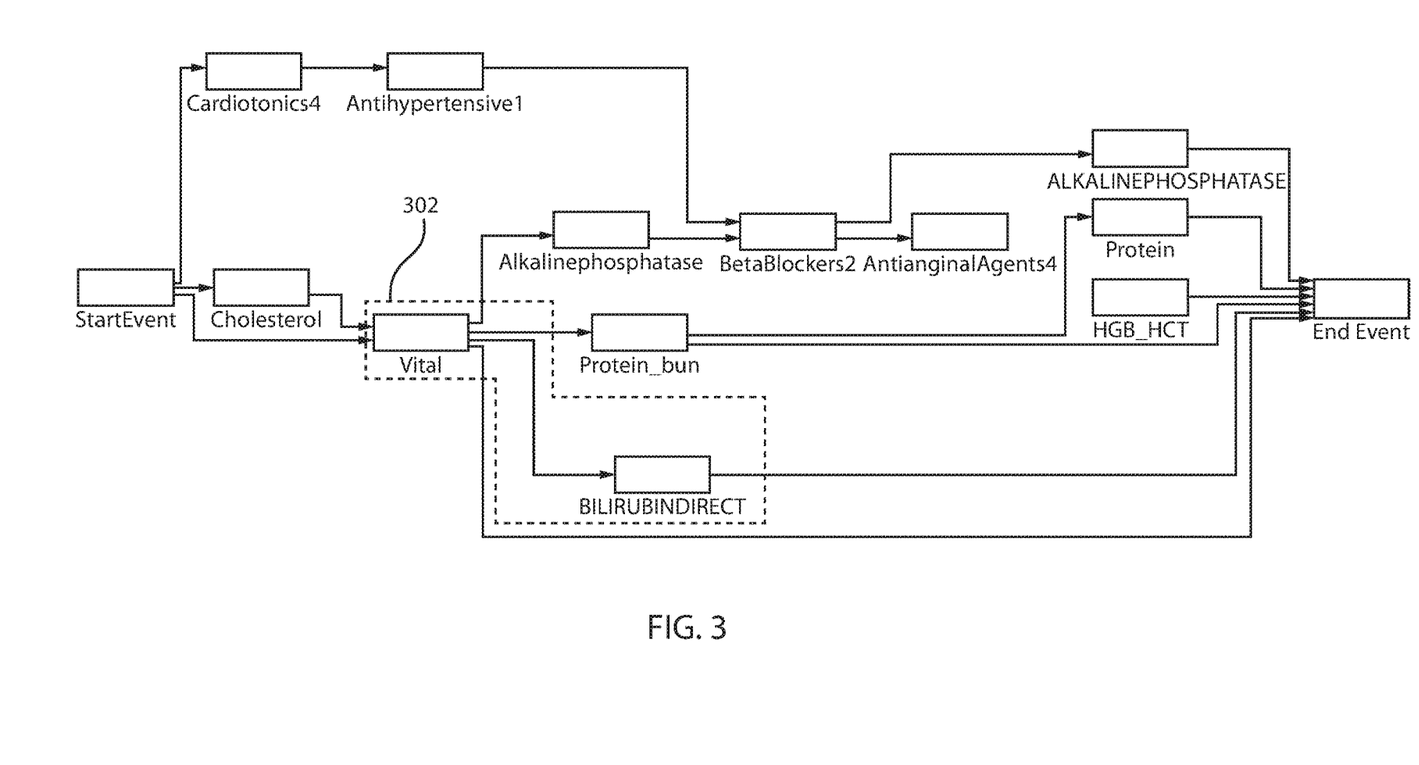
FIG. 3 shows an exemplary process model with a discriminative pattern overlaid, in accordance with one illustrative embodiment.

Referring for a moment to FIG. 3, a discriminative pattern is laid over a process model, in accordance with one illustrative embodiment. The discriminative pattern is identified in box 302, as the pattern from vital to BilirubinDirect. The discriminative pattern may be correlated with a positive patient outcome. For example, in one embodiment, the nodes of the discriminative pattern and edges connecting the nodes may be colored green to indicate the positive patient outcome.

The present principles provide a visual overlay of the discriminative patterns on a process model to enable a user to identify one or more discriminative patterns correlated with outcomes (e.g., positive or negative) in the context of the end-to-end clinical care pathways. Additionally, users can see the key clinical practice pathways correlated with outcomes on the mined model that represents an aggregation of all the clinical practice pathways. Insight can be obtained by comparing and contrasting separate overlays of clinical care pathways correlated to positive patient outcomes and negative patient outcomes.

Figure 4:
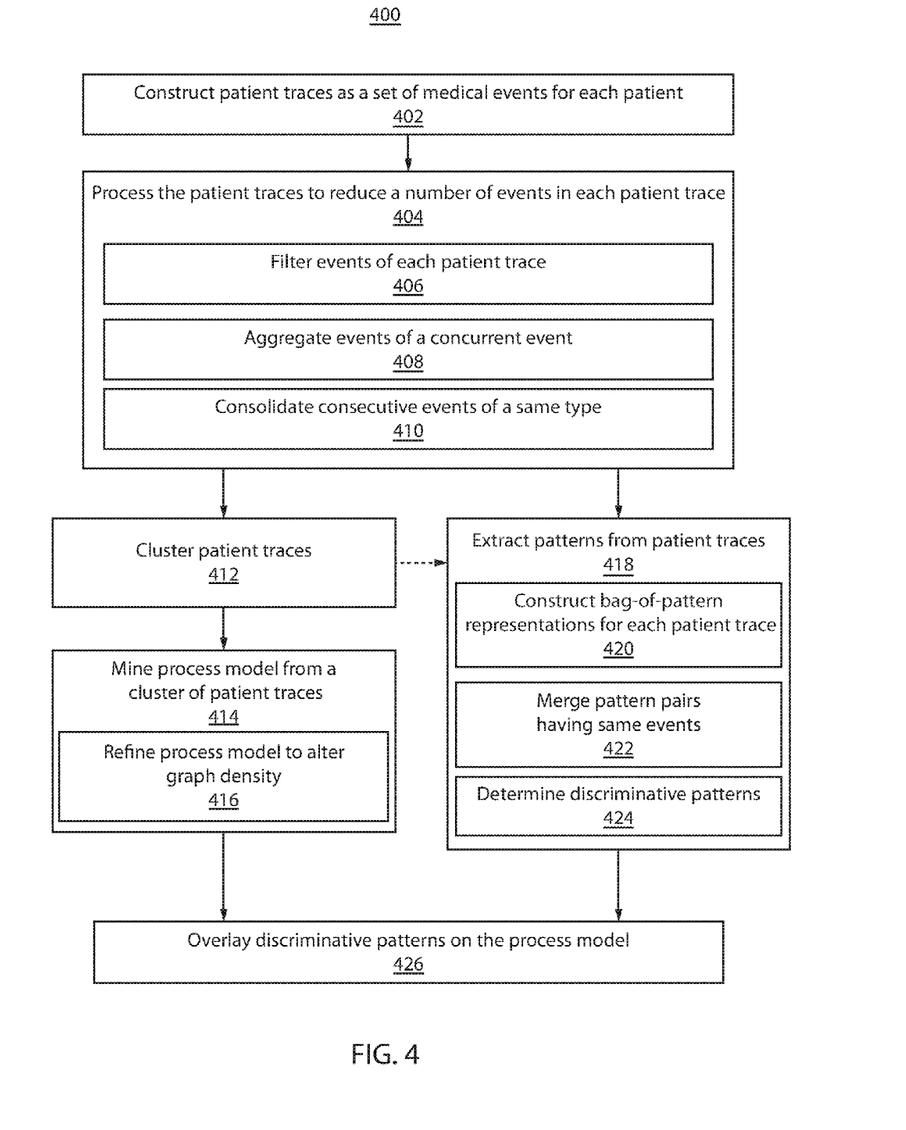
FIG. 4 is a block/flow diagram showing a system/method for extracting clinical care pathways correlated with patient outcomes, in accordance with one illustrative embodiment.

Referring now to FIG. 4, a block/flow diagram showing a method for extracting clinical care pathways correlated with outcomes 400 is depicted in accordance with one illustrative embodiment. In block 402, patient traces are constructed as a set of medical events for each patient. Patient medical information may be hierarchically stored as medical events, which may include, e.g., medications, labs, diagnoses, vital signs, etc. Patient traces may correspond to patient outcomes, which may be segmented, e.g., into positive and negative outcomes.

In block 404, the patient traces are processed to reduce a number of events in a patient trace. In block 406, events of the patient traces are filtered. Filtering may include, e.g., replacing event names with a hierarchical categorical name, filtering events of a patient trace by type or attribute, etc.

In block 408, events of a concurrent event may be aggregated to reduce the number of events in the concurrent event. Events occurring within a predefined time period (e.g., one day) may be represented as concurrent events. The number of events in a concurrent event may be reduced by first identifying event packages from the events in the concurrent event (e.g., by frequent itemset mining). A two-way sorting approach may be applied by first sorting event packages according to cardinality, and then sorting event packages with the same cardinality by appearance frequency. The event package with the longest cardinality is selected as a super event. If multiple event packages have the same longest cardinality, the event package with the longest cardinality that has the highest appearance frequency is selected as the super event. The process is repeated for the remaining events of the concurrent event.

In block 410, consecutive events of a same type are consolidated. Consecutive events of a same type preferably include consecutive identical events. The consolidated event may be distinguished by, e.g., adding the prefix "Rep," adding the suffice "-Repeat," etc.

In block 412, the patient traces are clustered. Clustering may include transforming patient traces into string-based representations and applying a string edit-distance metric. Clustering may include, e.g., DBSCAN, k-NN, etc. In block 412, a process model is constructed from a cluster of patient traces. The cluster may be the largest cluster, any cluster that includes a number of patient traces meeting or exceeding a threshold, etc. Constructing the process model may include adding a start event and end event in each patient trace. The start event has a timestamp that occurs before the earliest event in the patient trace. The end event has a timestamp that occurs after the latest event in the patient trace. The process model may be extracted by applying, e.g., HeuristicMiner in block 414.

In block 416, the process model is refined. In one embodiment, refining includes defining a dependence edge between two repeating event nodes according to the frequencies of the directions of dependencies for all of the repeating event nodes. The frequencies of the directions of dependencies may be compared to a threshold to define the direction of the dependency edge. In another embodiment, refining includes employing a minimum number of observations for showing a patient trace on the process model. Other methods of refining are also contemplated.

In block 418, patterns are extracted from patient traces. Preferably, patterns are extracted from the processed patient traces (in block 404). In other embodiment, patterns are extracted from a cluster of patient traces (in block 412). Pattern extraction may include any subsequence mining method, such as, e.g., prefix Scan, SPAM, etc. In block 420, patterns are represented as bag-of-pattern vectors for each patient trace. Events for a patient trace are collected into a pattern dictionary, including event and frequency of event occurrence. The entries of the bag-of-pattern vector indicate the frequency of appearance for the corresponding event of a patient trace. In block 422, pattern pairs having same events are merged and the dependency between the events is ignored. The frequency indicated in the bag-of-pattern vector for the resulting merged event is equal to the sum of the frequencies of each individual pattern it merged from.

In block 424, discriminative patterns are determined. Determining discriminative patterns may first include a preprocessing step to reduce the number of patterns based on, e.g., odds ratio, information gain, etc. Outcome analysis is performed on the remaining patterns by, e.g., sparse logistic regression to identify patterns most discriminative of a particular patient outcome.

In block 426, the discriminative patters are overlaid on the process model. Discriminative patterns may be represented to indicate patient outcome by, e.g., color.

Having described preferred embodiments of a system and method for extracting clinical care pathways correlated with outcomes (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A method for data analysis, comprising:
reducing medical events in one or more patient traces to provide processed patient traces;
mining a process model, using a processor, representing an aggregation of treatment pathways in the patient traces from a cluster of patient traces;
displaying, on a visual interface having a display, at least one of a plurality of patterns from the patient traces with respect to the process model to identify treatment pathways that are correlated with patient outcomes, the plurality of patterns being discriminative of patient outcomes and including at least one pattern associated with a positive patient outcome and at least one other pattern associated with a negative patient outcome; and
generating a refined process model of positive outcomes, wherein generating the refined process model includes varying a threshold on a minimum number of observations identified in the process mining and defining a dependence edge between two repeating event nodes according to one or more frequencies of directions of dependencies for the repeating event nodes; and
treating a particular disease associated with the medical events according to the generated refined process model, the generated refined process being further based on refining a care plan description according to treatment options for a particular patient according to the positive patient outcomes correlated to the treatment pathways.

2. The method as recited in claim 1, wherein said displaying step includes displaying the at least one of the patterns overlaid on the process model.

3. The method as recited in claim 1, wherein said displaying step includes displaying the at least one of the patterns with the process model based on the patient outcomes.

4. The method as recited in claim 1, wherein said displaying step includes highlighting nodes of the at least one of the patterns and edges between the nodes.

5. The method as recited in claim 1, wherein the cluster of patient traces includes at least one of a largest cluster of patient traces and a cluster having a number of patient traces meeting or exceeding a threshold number of patient traces.

6. The method as recited in claim 1, further comprising clustering the processed patient traces to identify the cluster of patient traces, wherein the clustering includes:
representing each patient trace of the processed patient traces as a string; and
computing a string edit distance between two patient traces of the processed patient traces to determine similarity between the two patient traces.

7. The method as recited in claim 1, wherein said mining step includes adding a start event and an end event to each of the patient traces.

8. The method as recited in claim 7, wherein the start event has a timestamp earlier than all other events in its patient trace and the end event has a timestamp later than all other events in its patient trace.

9. The method as recited in claim 1, wherein said mining step includes defining a dependency between repeating event node pairs according to a frequency of each direction of the dependencies from each of the repeating event node pairs.

10. The method as recited in claim 1, wherein said mining step includes representing medical events in the process model according to a frequency of appearance of medical events in the cluster of patient traces compared to a threshold.

11. The method as recited in claim 1, further comprising constructing the patient traces as a set of medical events for each patient of a patient population, the patient population being segmented based on patient outcomes.

12. The method as recited in claim 11, wherein said constructing step comprises constructing patient traces stored on a computer readable storage medium as a set of medical events for each patient of a patient population, the patient population being segmented based on patient outcomes.

13. The method as recited in claim 1, wherein said reducing step comprises aggregating events in a concurrent event to reduce a number of events in the concurrent event.

14. The method as recited in claim 13, wherein the number of events in the concurrent event are reduced by identifying event packages from the events in the concurrent event using frequent itemset mining.

15. The method as recited in claim 14, wherein the event packages are sorted according to cardinality and then the event packages with a same cardinality are sorted by appearance frequency.

16. The method as recited in claim 15, wherein, when multiple clinical event packages have a same longest cardinality, the event package with the same longest cardinality that has a highest appearance frequency is selected as a super event.

17. The method as recited in claim 1, wherein said mining step comprises refining the process model to alter a complexity of the process model.

18. The method as recited in claim 17, wherein said refining step comprises varying a dependency measure or a minimum number of observations.

19. The method as recited in claim 17, wherein said refining step comprises varying a threshold on a minimum number of observations identified in process mining to display a node of the process model.

20. The method as recited in claim 1, further comprising identifying patterns from patient traces that are discriminative of patient outcomes, wherein said identifying step includes applying hierarchical pattern summarization to compress a pattern set, and wherein hierarchical pattern summarization merges detected pattern pairs in a hierarchical way.

* * * * *